US006028234A

United States Patent [19]

Heinemann et al.

[11] Patent Number: 6,028,234

[45] **Date of Patent: *Feb. 22, 2000**

[54] PROCESS FOR MAKING GAS HYDRATES

[75] Inventors: Robert Frederick Heinemann; David Da-Teh Huang; Jinping Long, all of Plano, Tex.; Roland Bernard Saeger, Runnemede, N.J.

[73] Assignee: Mobil Oil Corporation, Fairfax, Va.

[ * ] Notice: This patent issued on a continued prosecution application filed under 37 CFR 1.53(d), and is subject to the twenty year patent term provisions of 35 U.S.C. 154(a)(2).

[21] Appl. No.: 08/766,983

[22] Filed: Dec. 17, 1996

[51] Int. Cl.[7] ................................ C07C 9/00; F17D 1/16; C10G 33/00

[52] U.S. Cl. ............................ 585/15; 585/950; 166/310; 166/371; 137/3; 137/13; 252/8.551; 62/45.1; 95/153; 208/187

[58] Field of Search ..................... 585/15, 950; 166/310, 166/371; 137/3, 13; 252/8.551; 62/45.1; 95/153; 208/187

[56] References Cited

U.S. PATENT DOCUMENTS

| | | | |
|---|---|---|---|
| 2,270,016 | 1/1942 | Benesh . | |
| 2,375,559 | 5/1945 | Hutchinson et al. . | |
| 2,904,511 | 9/1959 | Donath . | |
| 3,170,870 | 2/1965 | Bachman . | |
| 3,514,274 | 5/1970 | Cahn et al. . | |
| 3,856,492 | 12/1974 | Klass . | |
| 3,888,434 | 6/1975 | Chersky et al. . | |
| 3,954,921 | 5/1976 | Yoshida et al. . | |
| 3,975,167 | 8/1976 | Nierman . | |
| 4,915,176 | 4/1990 | Sugier et al. | 166/371 |
| 4,920,752 | 5/1990 | Ehrsam | 62/46.1 |
| 4,930,319 | 6/1990 | Bee et al. | 62/69 |
| 5,473,904 | 12/1995 | Guo et al. | 62/46.1 |
| 5,536,893 | 7/1996 | Gudmundsson | 585/15 |
| 5,562,891 | 10/1996 | Spencer et al. | 423/437 R |

FOREIGN PATENT DOCUMENTS

WO 93/01153 1/1993 WIPO .

OTHER PUBLICATIONS

1936 Index To Refiner And Natural Gasoline Manufacturer, A Gulf Publishing Company Publication, "*The Solvent Dewaxing Process*", by W. P. Gee, et al.., vol. 15, Jun. 1936 (pp. 205–209).

American Gas Association Monthly, Feb. 1946, vol. 28, No. 2, *Hydrate Storage of Natural Gas,* by Benjamin Miller, et al., (pp. 63–67, p. 92).

Handbook of Natural Gas Engineering, Chapter 5, "*Water–Hydrocarbon Systems*", by Donald L. Katz (pp. 189–221) no date available.

Chemical Engineering Science, vol. 42, No. 7, 1987 "*Kinetics of Methane Hydrate Decomposition*", by H. C. Kim, et al., (pp. 1645–1653) no month available.

Soviet Geology and Geophysics, "*The Dynamics of the Zone of Hydrate Formation and its Effect on the Temperature Regime of the Cryolithozone*", by A. A. Trofimuk, et al., vol. 27, No. 11, 1986 (pp. 1–7) no month available.

Newscientist, "*Gas Hydrates Keep Energy On Ice*", by Ian Ridley et al., Feb. 25, 1988 (pp. 53–58).

Theoretical Foundations of Chemical Engineering, Translated from Russian, "*New Technologies Using Gas Hydrates*", by L. F. Smirnov, vol. 23, No. 6, Nov.–Dec. 1989 (pp. 514–526).

Inzbenernay A Geologiy A, "*Experimental Investigations of the Microstructure of Agglomerate of Ice and Methane Hydrate*", by E. D. Ershov, et al.. No. 3, (pp. 32–37) 1990 no month available.

The State–of–the–Art of Hydrates as related to the Natural Gas Industry Final Report (Jan. 1990–Oct. 1991) Part 4. of a Project Entitled "*The Economic Impact of Fluid Properties Data on the Gas Industry*" by E. Dendy Sloan, Jr. for Gas Research Institute Contract Number 5086–260–1212, Jun. 1, 1992 (pp. 1–34).

Cold Regions Science and Technology, 20 (1992), Elsevier Science Publishers B.V., Amsterdam, "*Experimental Research on Gas Hydrate Decomposition in Frozen Rocks*", by E. D. Ershov, et al.. (pp. 147–156) no month available.

Industrial & Engineering Chemistry Research, A publication of the American Chemical Society, Jul. 1993, 32 "*Clathrate Hydrates*", by Peter Englezos (pp. 1251–1274).

SPE Production & Facilities, "*Storing Natural Gas as Frozen Hydrate*", by J. S. Gudmundsson, et al., Feb. 1994, vol. 9, No. 1 (pp. 69–73).

Annals of the New York Academy of Sciences, vol. 715, "*Overview—Gas Hydrate Geology and Geography*" by Rodney D. Malone (pp. 225–231) (1994) no month available.

Annals of the New York Academy of Sciences, vol. 715, "*Natural Gas Hydrate Occurrence and Issues*", by Keith A. Kvenvolden (pp. 232–246) (1994) no month available.

The Proceedings of the Fifth (1995) International Offshore and Polar Engineering Conference, vol. 1, 1995 "*Transport of Natural Gas as Frozen Hydrate*", by J. S. Gudmundsson, et al. (pp. 282–288). no month available.

Advanced Technology, Leonard LeBlanc, Houston, "*Natural Gas Transport as Hydrates 25*
Below Cost of LNG". no date available.

McGraw–Hill Book Company, Third Edition, by Max S. Peters, et al., "*Plant Design and Economics for Chemical Engineers*" (pp. 575–586) (1980) no month available.

*Primary Examiner*—Elizabeth D Wood
*Attorney, Agent, or Firm*—Robert B. Furr, Jr.; Malcolm D. Keen

[57] ABSTRACT

The present invention provides a process for continuously producing clathrate hydrate. This process includes comprising the steps of:

(a) pressurizing a hydrate-forming gas to an elevated pressure and cooling the hydrate-forming gas below the gas-water-hydrate equilibrium point at the elevated pressure;

(b) cooling liquid water below the gas-water-hydrate equilibrium temperature for the elevated pressure;

(c) charging hydrate-forming gas at the elevated pressure into a reaction zone which contains a movable surface;

(d) atomizing water in the reaction zone in contact with the hydrate-forming gas to form gas hydrates in the reaction;

(e) depositing the gas hydrates on the movable surface; and (f) collecting the gas hydrates from the movable surface.

20 Claims, 3 Drawing Sheets

Hydrate Production Method

Hydrate Production
Apparatus 600 (gas-continuous)

Hydrate Production
Apparatus 600 (water-continuous)

PROCESS FOR MAKING GAS HYDRATES

FIELD OF THE INVENTION

This invention relates to a method of continuous production of clathrate gas hydrates, specifically natural gas and their associated gas mixtures and other hydrate forming gases; and an apparatus therefor. This invention also relates to a method of continuous separation of hydrate from water and gas in the same apparatus.

BACKGROUND OF THE INVENTION

Gas hydrate is a special type of inclusion compound which forms when light hydrocarbon ($C_1$–$C_4$) constituents and other light gases ($CO_2$, $H_2S$, $N_2$, etc.) physically react with water at elevated pressures and low temperatures. Natural gas hydrates are solid materials, and they do not flow readily in concentrated slurries or solid forms. They have been considered as an industrial nuisance for almost sixty years due to their troublesome properties of flow channel blockage in oil and gas production and transmission systems. In order to reduce the cost of gas production and transmission, the nuisance aspects of gas hydrates have motivated years of hydrate inhibition research supported by the oil and gas industry. (Handbook of Natural Gas, D. Katz etc., pp. 189–221, McGraw-Hill, New York, 1959; Clathrate Hydrates of Natural Gases, E. D. Sloan Jr., Marcel Dekker, Inc. 1991). The naturally occurring natural gas hydrates are also of interest as an alternative energy resource for the industry. (International Conferences on Natural Gas Hydrates, Editors, E. D. Sloan, Jr., J. Happel, M. A. Hnatow, 1994, pp. 225–231—Overview: Gas Hydrates Geology and Geography, R. D. Malone; pp. 232–246—Natural Gas Hydrate Occurrence and Issues, K. A. Kvenvolden).

Natural gas hydrates contain as much as 180 standard cubic feet of gas per cubic foot of solid natural gas hydrates, and several researchers have suggested that hydrates can be used to store and transport natural gases. (B. Miller and E. R. Strong, *Am. Gas. Asso. Mon* 28(2), 63-1946). The high concentration of gas in the hydrates has led researchers to consider intentionally forming these materials for the purpose of storing and transporting natural gases more safely and cost effectively. U.S. Pat. No. 5,536,893 to Gudmundson discloses a multi-stage process for producing natural gas hydrates. See also Gudmundsson, et al., "Transport of Natural Gas as Frozen Hydrate", ISOPE Conf. Proc., V1, The Hague, NL, June, 1995; "Storing Natural Gas as Frozen Hydrate", SPE Production & Facilities, Feb. 1994.

U.S. Pat. No. 3,514,274 to Cahn et al. teaches a process in which the solid hydrate phase is generated in one or a series of process steps and then conveyed to either storage or directly to a marine transport vessel. This process requires conveyance of a concentrated hydrate slurry to storage and marine transport. Pneumatic conveyance of compressed hydrate blocks and cylinders through ducts and pipelines has also been proposed. See Smirnov, L. F., "New Technologies Using Gas Hydrates", Teor. Osn. Khim. Tekhnol., V23(6), pp. 808–22 (1989), application WO 93/01153, Jan. 21, 1993.

Based upon the published literature (E. D. Sloan, 1991 Clathrate Hydrates of Natural Gases, Marcel Dekker), transporting a concentrated gas hydrate slurry in a pipe from a stirred-tank vessel would appear to be incompatible with reliable operation, or even semi-continuous operation. The blockage of pipes and fouling of the reactors and mixing units are the critical issues. Improved chemical and/or mechanical methods to prevent gas hydrate blockage and fouling remain the focus of current gas hydrate research.

(Long, J. "Gas Hydrate Formation Mechanism and Kinetic Inhibition", PhD dissertation, 1994, Colorado School of Mines, Golden, Colo.; Sloan, E. D., "The State-of-the-Art of Hydrates as Related to the Natural Gas Industry,", Topical Report GRI 91/0302, June, 1992; Englezos, P., "Clathrate Hydrates", Ind. Eng. Chem. Res., V32, pp 1251–1274, 1993).

Gas hydrates are special inclusion compounds having a crystalline structure known as clathrate. Gas molecules are physically entrapped or engaged in an expanded water lattice network comprising hydrogen-bonded water molecules. The structure is stable due to weak van der Waals' forces between gas and water molecules and hydrogen-bonding between water molecules within the cage structures. A unit crystal of structure I clathrate hydrates comprises two tetrakaidecahedron cavities and six dodecahedron cavities for every 46 water molecules, and the entrapped gases may consist of methane, ethane, carbon dioxide, and hydrogen sulfide. The unit crystal of structure II clathrate hydrates, on the other hand, contains 8 large hexakaidecahedron cavities and 16 dodecahedron cavities for every 136 water molecules.

SUMMARY OF THE INVENTION

The present invention provides a process for continuously producing clathrate hydrate comprising the steps of:

(a) pressurizing a hydrate-forming gas to an elevated pressure and cooling said hydrate-forming gas below the gas-water-hydrate equilibrium point at said elevated pressure;

(b) cooling liquid water below the gas-water-hydrate equilibrium temperature for said elevated pressure;

(c) charging hydrate-forming gas at said elevated pressure into a reaction zone which contains a movable surface;

(d) atomizing water in said reaction zone in contact with said hydrate-forming gas to form gas hydrates in said reaction zone;

(e) depositing said gas hydrates on said movable surface; and (f) collecting said gas hydrates from said movable surface.

The pressure in the reaction zone is at least sufficient to form said gas hydrates, and the temperature is low enough to form said gas hydrates with respect to the hydrate thermodynamic equilibrium point for a mixture of water and the hydrate-forming gas. The process of the invention preferably further includes atomizing and spraying water and gas into the reaction zone and on the movable surface. The process may optionally further include flowing a chilled, pressurized natural gas mixture onto the movable surface at a point on the movable surface before the point at which the gas hydrates are collected. The movable surface in the hydrate production system can be a smooth and/or rough surface with relatively high energy and active nucleation sites. Suitable movable surfaces include metallic or non-metallic surfaces, or surfaces containing sand, zeolite or similar additives or impurities to promote the gas hydrate formation. The movable surface can also be permeable or impermeable with respect to water flow. The collecting step (f) typically further comprises scraping or otherwise removing said gas hydrates from the movable surface, and may optionally further comprise crushing the hydrate. During the collection step, the hydrate may be further dried by blowing chilled natural gas mixtures onto the hydrate. The collected hydrate may then be withdrawn from the reaction zone, preferably through an outlet section which is blanketed with an non-explosive gas mixtures, such as inert gases, flue gases, non-flammable natural gas mixtures, or stock gases with very low oxygen contents (for example less than 4%).

The process of the invention continuously produces gas hydrates from a suitable hydrate-forming gas (e.g., natural gas mixtures) and water. In one embodiment, the process is useful in the storage and transportation of natural gas, as an alternative to pipeline or liquefied natural gas (LNG). In another embodiment, the process can be used to continuously produce gas hydrates for the purpose of gas separation by hydrates, desalination, or other gas hydrate production. Useful water-containing feedstocks include both fresh or pure water, salt water (e.g. seawater), and any water contaminated by particulates or other materials. The gas used to form hydrates can be pure hydrocarbon gases ($C_1$–$C_4$), natural gas mixtures, and other hydrate forming gases, such as nitrogen, carbon dioxide, hydrogen sulfide etc. The gas may be contaminated by other impurities, such as particulates and other non-hydrate forming materials and compounds. In a preferred embodiment, the process of the invention separates the gas hydrates using a rotary drum as the movable surface. This embodiment provides essentially single-step production and separation, thus minimizing equipment size and cost; a substantial technical and economic advantage in shipboard or on-platform applications for remote, offshore gas accumulations, including associated gas in oil production. Other examples of rotary-drum vessels are used in spray dryers (Peters, M. S., and Timmerhaus, K. D., "Plant Design and Economics for Chemical Engineers", 4th edition, McGraw-Hill, 1991) and lubricant oil solvent dewaxing units ("Petroleum Refiner", V. 15 (6), pp. 205–209, June, 1936). Three principal advantages of the present inventive process over previously known hydrate production methods include (a) hydrate production/separation is carried out in one vessel, minimizing capital cost, (b) no concentrated slurry transportation, and (c) hydrate conveyance is limited to one solid stream exiting the production zone.

The present invention provides a method for the continuous production of gas hydrates from water and hydrate forming gases, such as $CO_2$, $H_2S$, natural gas, and associated natural gas, just to mention a few. However, in the following, natural gas is in general described as the gaseous component in the production process, but it should be evident that a person skilled in the art can apply the principle of the invention to consider hydrate forming gases other than natural gas, and the invention should for that reason not be regarded as limited to use of natural gas only. The present method for production of gas hydrates can be adapted to both onshore and offshore operation.

Feedstocks

Useful water-containing feedstocks include both fresh or pure water (e.g., lake or river water) and salt water (e.g. seawater). Water contaminated by particulates or other materials, such as formation water from oil production, may also be used. The gas feed stock used to form hydrates can be pure hydrocarbon gases ($C_1$–$C_4$), natural gas feedstock mixtures, and other hydrate forming gases such as oxygen, nitrogen, carbon dioxide, and hydrogen sulfide and their respective mixtures. The gas may be contaminated by other impurities, such as particulate and other non-hydrate forming materials or compounds. Both feedstocks should preferably be pressurized to sufficiently high pressure and chilled to sufficiently low temperature before their entering the gas hydrate production (reaction) zone, and preferably both water and gas are suitably atomized/sprayed into small drops and distributed in the reaction zone and on the movable surface.

Process Conditions

| | Temperature, ° C. | | | Pressure, kPa | | |
|---|---|---|---|---|---|---|
| | Useful | Preferred | More Preferred | Useful | Preferred | More Preferred |
| Hydrate Formation Stage | −10 to 25 | −5 to 15 | −3 to 5 | 100 to 100000 | 500 to 10000 | 500 to 5000 |
| Freezing Stage | −30 to 0 | −20 to 0 | −20 to −5 | 100 to 500 | 100 to 300 | 102.5 to 200 |

The process conditions within the gas hydrate formation section are preferably controlled at relatively constant pressure and temperature. The inlet pressure of the water and gas are determined by the rate of hydrate formation in order to have steady-state conditions for pressure, temperature, and hydrate production rates. In one preferred embodiment, a selectively permeable material is used for the movable surface. The pressure in the hydrate formation section should be maintained at gas hydrate formation conditions. The pressure difference ($\Delta P$) across the permeable surface can be as small as 0.1 kPa or as high as 10000 kPa.

| | Temperature, ° C. | | | Pressure, kPa | | |
|---|---|---|---|---|---|---|
| | Useful | Preferred | More Preferred | Useful | Preferred | More Preferred |
| Inside Accumulator Drum | −10 to 25 | −5 to 15 | −3 to 5 | 0.1 to 10000 | 10 to 5000 | 100 to 1000 |

Movable Surface Description

The movable surface in the hydrate production system can be a smooth surface, a rough surface with high energy and active nucleation sites, or a combination of smooth and rough surfaces. Suitable movable surfaces include metallic or non-metallic surfaces, any surfaces deposited by sand, zeolite or another suitable impurity which can promote the gas hydrate formation, and preferably comprise metal surfaces with a high tensile strength. The movable surface can also be permeable or impermeable with respect to water flow.

Detailed Process Description

Figure 1:
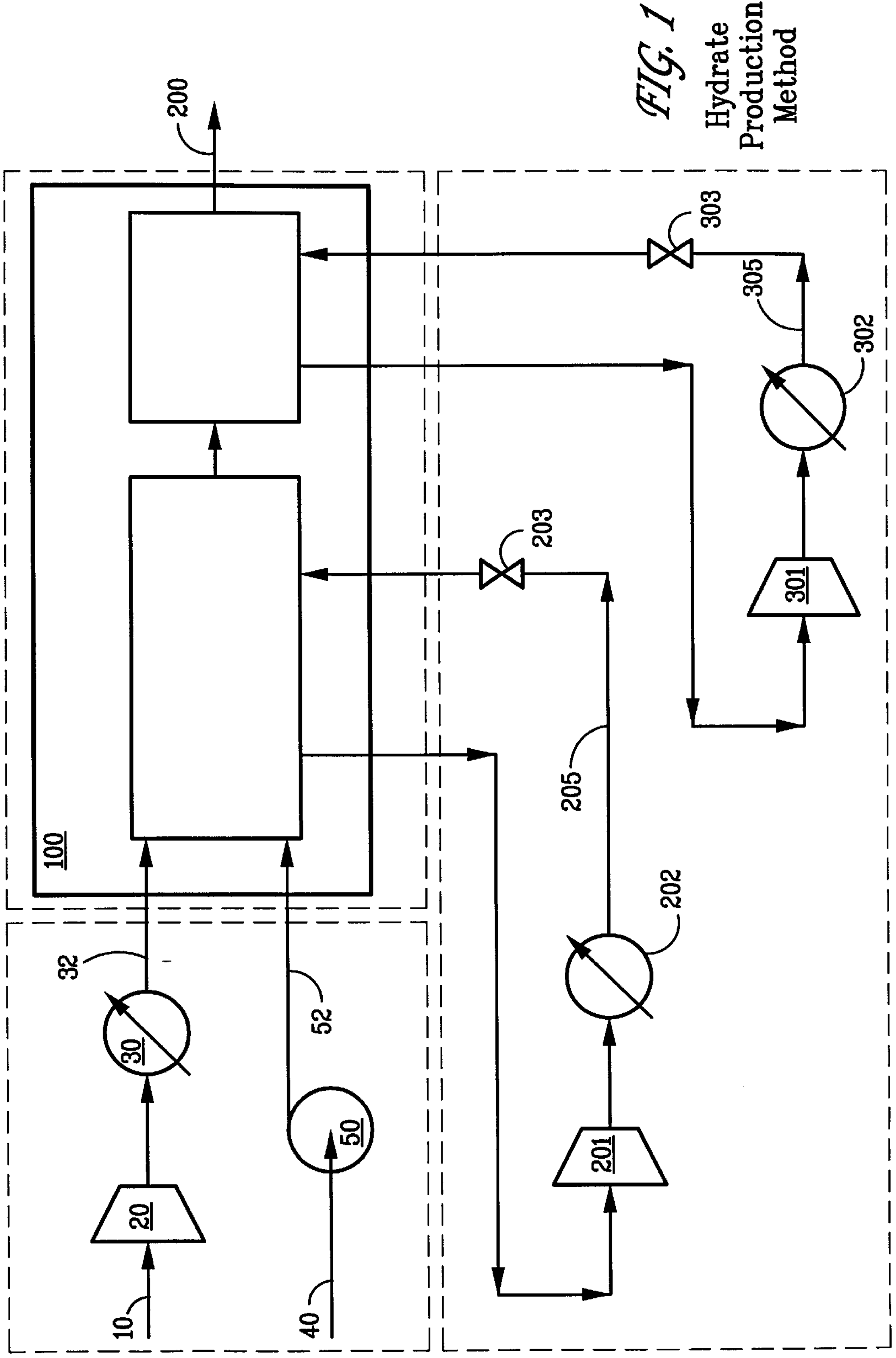
FIG. 1 is a simplified schematic diagram showing a gas hydrate production process with recirculation and cooling/drying operations.

Referring now to FIG. 1, the cooled natural gas stream 10 is charged to compressor 20, where is it compressed to a pressure as specified in the process condition table. An aftercooler 30 chilled the temperature of the compressed natural gas stream to the process conditions as specified in the process condition table. Meanwhile, a water stream 40 at ambient pressure and a temperature close to hydrate formation condition flows to a feed pump 50, increasing the water stream's pressure to no more than about 1500 kPa higher than that of the compressed natural gas 32. The water stream 40 may be fresh water, sea water, or a mixture in any proportion of fresh and sea water with some impurities such as particulates or other dissolved chemicals.

The water stream 52 and compressed natural gas stream 32 are co-fed to a gas hydrate production apparatus 100, which produces a stream of frozen gas hydrate 200 at 1 atm pressure, absolute, and from about −18 to about −12° C. The gas hydrate production apparatus is cold-traced with refrigerant loops at two temperature levels: from about −6 to about 16° C. in refrigerant stream 205, and from about −24 to about—−18° C. in stream 305. Each refrigerant loop is comprised of a compressor (201, 301), intercooler (202, 302) and throttling valve (203, 303). Refrigerant in each loop can be HCFCs (e.g. R-12, HFC-134a), HFCs (e.g. R-22, R407C, R-502, HFC404A), hydrocarbons (e.g. propane, iso-butane), or ammonia.

Figure 2:
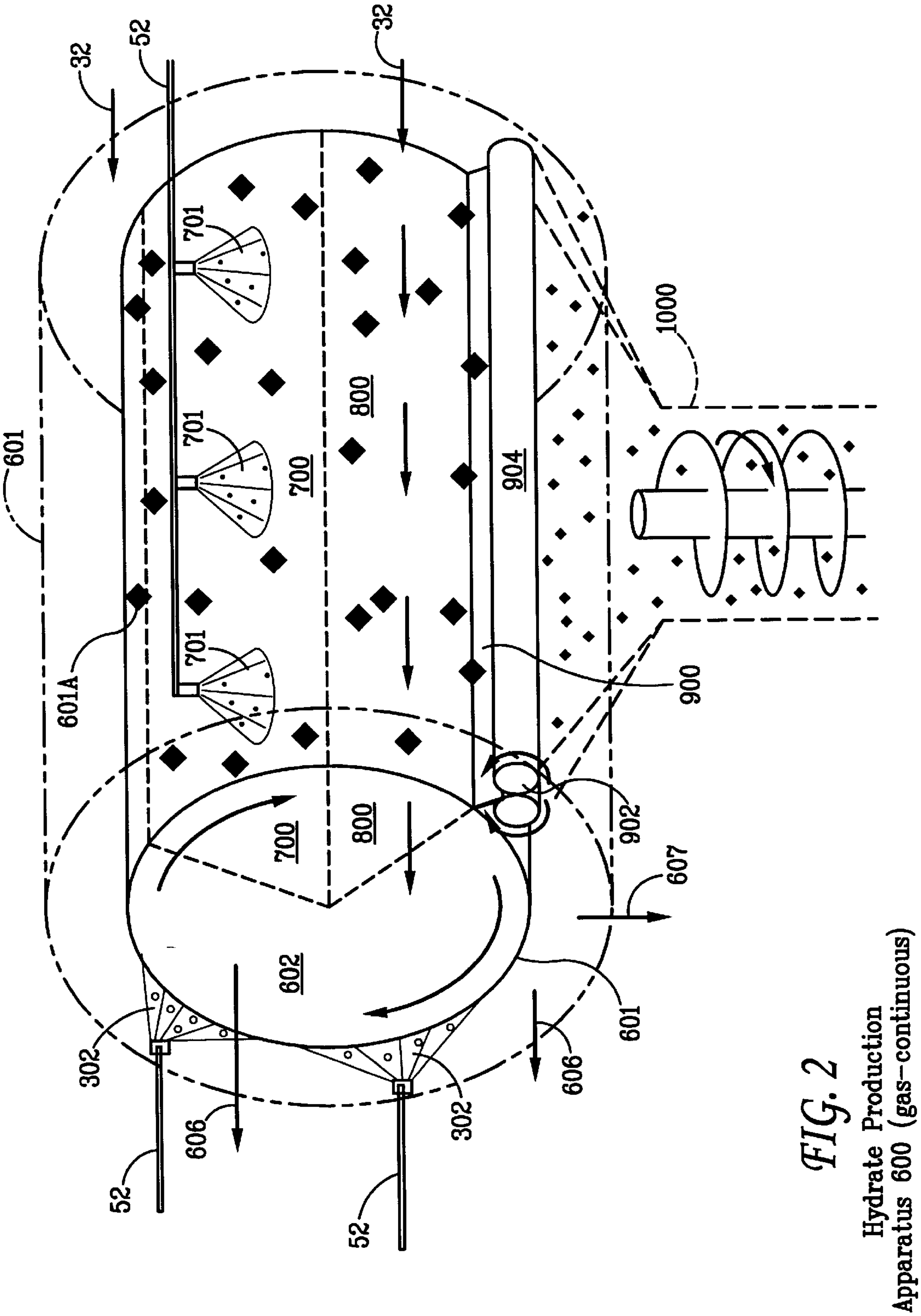
FIG. 2 is a simplified schematic in perspective view showing selected processing steps in one embodiment of the present invention, namely gas continuous hydrate production.

FIG. 2 shows one possible embodiment of the gas hydrate production apparatus—gas water continuous hydrate production. The high-pressure water stream 52 enters formation section 601 of hydrate production apparatus 600 through spray nozzles 302. These spray nozzles atomize the water into drops with diameters of 1–1000 microns in diameter. Examples of commercial nozzles capable of generating desired water sprays include Bete Fog series NF3000-6000 (manufactured by the Bete Fog Corporation), or the Whirljet and Fulljet series nozzles (manufactured by Spraying Systems, Inc.).

The compressed natural gas stream 32 enters formation section 601 axially or circumferentially through one or more ports, or one or more distributor manifolds to distribute gas uniformly throughout formation section 601, which is maintained at a pressure of from about 790 to about 10,500 kPa and a temperature of from about 0 to about 21° C. The nozzles may be distributed around the drum selectively in order to have the optimum efficiency. For example, gas nozzles may concentrate gas flow at one side of the drum in order to dry the produced gas hydrates.

The compressed gas may be charged to the reactor separately from the water feed, or optionally may be pre-mixed with the water feed and charged to the reactor 600 through suitable spray nozzles. The temperature in formation section 601 is maintained by cold tracing (not shown) connected to the high-temperature refrigeration loop (FIG. 1). Excess water leaves the bottom of the formation section 601 through a drain 607. Excess gas 606 is removed from the formation section 601 through ports or manifolds.

The water and the gas react almost immediately on contact to produce natural gas hydrate. The pressure and temperature conditions in the reactor are adjusted to favor hydrate formation, and the gas pressure prior to expansion is preferably adjusted to provide cooling during expansion by means of the Joule-Thomson effect. Provided that there is a defined ratio between pressure and temperature that represents equilibrium between gas hydrate and water, the reactor temperature is preferably decreased a few degrees below the equilibrium temperature, thus increasing the reaction rate for the formation of natural gas hydrate. A sub-cooling from 1° to 10° C. is in most cases sufficient, and a typical sub-cooling varies from 2° to 6° C. In a preferred embodiment of the present invention, gas hydrates are generated, concentrated and purified in one apparatus: a rotary-drum vessel.

Because of their small size and large gas/water interfacial area, the water drops and dissolved natural gas form hydrates 601A either in the bulk gas, or upon contact with the movable surface 602, which can be a rotating drum, as shown in FIG. 2, conveyor belt, or a reciprocating surface. Likewise, the cross-section of formation section 601 may be either cylindrical or another configuration as dictated by the configuration of the movable surface 602. The material comprising the movable surface may be smooth, or rough with high energy and active nucleation sites. The movable surface may be metallic or non-metallic, smooth or rough, or any surface deposited by sand, zeolite or other impurity which can promote gas hydrate formation. The movable surface may be permeable or impermeable to gas and/or water flow. Pressure drop across a permeable surface may range from negligible to the entire gauge pressure of formation section 601.

Hydrates 601A adhere to the movable surface 602 by adhesion and gas/water flow through the movable surface 602, if it is permeable to water and/or gas flow. Optionally, a water wash zone 700 is equipped with spray nozzles 701 to spray excess water onto the hydrate crystals to remove precipitates (e.g. salt and debris). Optionally, hydrates are dried in a gas drying zone 800, where excess gas contacts hydrates adhering to the movable surface 602. The gas entering the gas drying zone may do so either through the same or separate ports or gas distribution manifolds as mentioned above. The gas entering the gas drying zone may be prechilled by the low-temperature refrigeration loop (see FIG. 1) to assist in stabilizing the frozen hydrate.

A doctor blade 900 mechanically removes the hydrate crystals from the movable surface 602, where they are crushed by a pair of rotating rollers or grinders 902, 904. The rollers are preferably coated with a flexible material (e.g. rubber, polymer composite) to assist in creating a high-pressure seal between formation section 601 and the freezing zone 1000.

Because the hydrate crystals entering the freezing zone are well-above their metastable temperature, the freezing zone 1000 must be maintained at hydrate formation pressure (from about 790 to about 10,500 kPa) to avoid decomposition. A screw conveyor 1010 moves hydrates out of the apparatus to storage or ship/barge loading. A second pair of rotating rollers or grinders (not shown) at the exit of the freezing zone creates a seal between the high-pressure atmosphere of the freezing zone and the low-pressure exit. The freezing zone 1000 is maintained at hydrate metastable temperature (from about −18 to about −12° C.) by either cold-tracing connected to the low-temperature refrigeration loop (FIG. 1), or chilled gas that is circulated throughout the freezing zone. The chilled gas making up the atmosphere in the freezing zone must contain less than 3 v. % oxygen to prevent explosion, and may contain other any mixture of non-condensibles such as natural gas, nitrogen, carbon dioxide or noble gases (helium, neon, argon, etc.).

Figure 3:
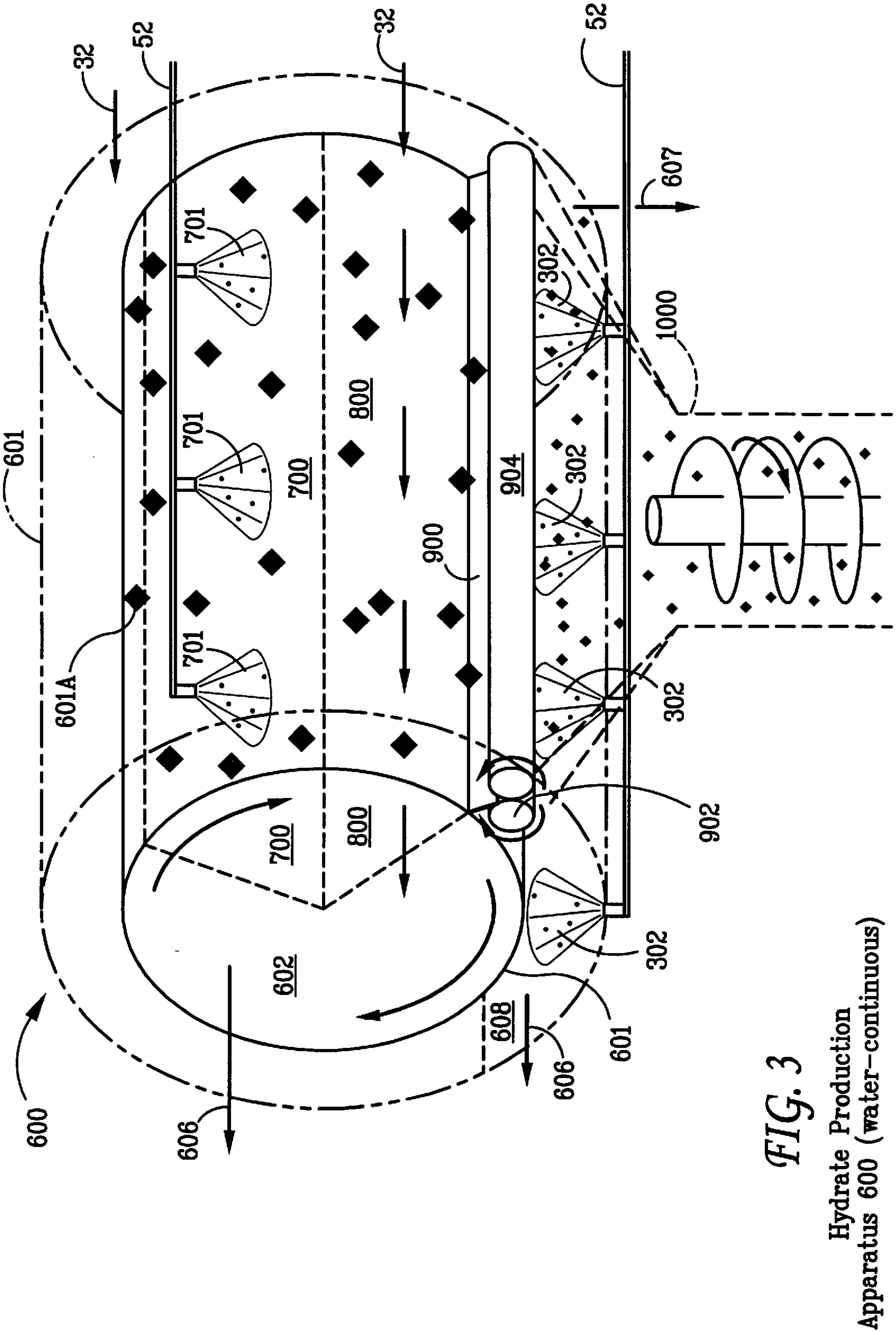
FIG. 3 is a simplified schematic in perspective view showing selected processing steps in another embodiment of the present invention, namely water continuous hydrate production.

A second embodiment of the hydrate production apparatus 600 is shown in FIG. 3—water continuous hydrate production. This embodiment is distinct from that in FIG. 2 in that gas hydrate formation is promoted by atomizing gas through spray nozzles 302 in a water continuum 608 located at the bottom of the of the formation section 601. In this embodiment, the high-pressure water stream is fed to the bottom of the formation section 601 by either one or more ports or distribution manifolds. The pressure of the compressed natural gas stream 32 is no more than 200 psi above that of the formation section 601. Excess water leaves the bottom of the formation section 601 through a drain 607. Aside from the features noted above, the water-continuous embodiment of the hydrate production apparatus can be described as was done above for the gas continuous embodiment shown in FIG. 2.

A potential advantage of the water-continuous embodiment over the gas-continuous embodiment noted above is that in the case of a water feed containing salt, the salt concentration in the water leaving the hydrate production apparatus through the drain 607 is higher than that in the gas hydrates. Thus, the hydrate formation apparatus 601 also performs desalination.

The solid hydrate particles can be used for storage and transportation of gases. They can also be used for operating transporting means onshore and offshore. Other gases may also be used to produce the solid hydrate particles. These other gases can be commercial products or pollutants or other gas types that form in natural or industrial processes. Solid hydrate particles can be used in power stations and in processes intended for reduction of pollution. Solid hydrate particles can be used where gas has to be added in large amounts, in aquatic environments, both natural and artificial.

The solid particles can be stored in offshore platforms in sub-sea vessels under pressure. These vessels can be located on the sea bed or adjacent to the platform. They can be pressurized hydrostatically with a water column through a valve arrangement with a manometer to keep the vessel and the sea water separated by means of a water column. The solid particles can be stored as solid material in gas or surrounded by cooled water or a hydrocarbon based liquid. In addition to sub-sea vessels, tankers, barges, and the like can be used, or submerged vessels made up of a stiff or flexible material.

Hydrate particles with embedded gas can be transported from offshore storage vessels by boat, tankers, barges or floating containers towed by tugboats to the shore. In the most preferred arrangement, hydrate particles are transferred from the storage vessels offshore through a pipeline or a mechanical conveyor to a tanker by a combination of screw conveyors and gravity feed. The tanker may, but does not need to, be able to store the particles under gauge pressure. The particles can be transported to the shore as solid cargo or in water or in a hydrocarbon based liquid. Gas that escapes from the particles during transportation can be pressurized and/or used to operate the tanker and the cooling equipment, or other means to dispose of the extra gas can be used.

Hydrate particles can also be stored in underground storage rooms, such as large caverns blown in rock formations. This can be accomplished by cooling/refrigerating the underground storage cavern prior to the supply of gas hydrates, so that any naturally occurring water freezes and forms an isolating ice shell on the "vessel" walls. In this way, gas escape from the storage cavern can be prevented. Like ordinary isolated vessels, the gas hydrate produced in accordance with the invention can be stored near atmospheric pressure, as described in further detail below.

After transportation, the hydrate particles with embedded gas are pumped or transferred by other ways, such as screw conveyor from the tanker to one or several storage tanks onshore. The gas may also be recovered by insitu onboard regassifications. The melting can be accomplished using different types of heating, e.g. with emission from a gas operated power station, or the hot water exit from the turbine engine. Cold melting water can be used as coolant for any power station, thus improving the efficiency of an ordinary cooling tower.

When the tanker is emptied, melting water and process water can be loaded. The water can have its origin from a former cargo. The melting water will be ballast for the tanker from the shore to an offshore platform. When the tanker loads the particles at the platform, the melting water is unloaded. The vessels at the platform accept the melting water for use in the hydrate production. If desired, air may be removed from the melting water and the process water and optionally pre-treated. The air removal can be effected onshore and/or offshore. In addition, the water can be used for injection to a reservoir.

The water pressure is critical for the formation of gas hydrate, and the pressure can be adjusted to a desired level provided that the pressure is higher than the reactor pressure (above the hydrate equilibrium pressure at a specific temperature). However, the water pressure should be adjusted to achieve sufficient volumetric injection of water to the reactor and properly dispersing the water in the gas phase as fine droplets. Because of the exothermic character of the formation reaction, it is preferred that the construction and the operation conditions, particularly the pressure, is chosen to provide the best possible cooling of the feed streams. This is accomplished by adjusting the pressure of the gas supplied to the reactor vessel to provide cooling by expansion (Joule-Thomson effect), and the expansion is in this case also carried out by means of nozzles. Moreover, it is favorable to adjust the reactor temperature a few degrees below the hydrate equilibrium temperature, generally from about 1° to about 10° C., preferably 2° C. to 6° C., thus increasing the rate of hydrate formation. The formation rate can also be increased by adding small seeds of hydrate crystals to the water to be supplied to the reactor so that hydrate can more easily grow from these in the reactor. The formation of hydrate nuclei occurs at the interface between the water and the gas bulk phase. The water is, therefore, preferably dispersed as thoroughly as possible in the gas bulk phase. The water can be supplied to the reactor through the same openings, e.g. nozzles, as the gas, thus establishing a mixing effect at the supply location in the reactor. Moreover, water droplets in the reactor can be dispersed in the gas bulk phase by, for example, a spreader means, such as a rotating plate with nozzles distributing fine droplets (preferably having a diameter on the order of a micrometer), or by using physical guiding or blocking means inside the reactor, or by using a stirrer (not shown). Recirculated un-reacted gas can also be supplied to the reactor perpendicular to the main flow of fresh gas feed, thus achieving even better mixing of the reactants. However, the reactor pressure and the respective initial pressures for gas and water can be determined as desired, depending on the total pressure loss in the system and the gas pressure available. With respect to the process heat balance, a general rule says that the lower the reactor pressure, the less energy is required to produce gas hydrates based on the total energy content in the hydrate. On the other hand, the reaction rate for the formation of gas hydrate will increase with the pressure, and accordingly the reactor pressure must also be adjusted in view of the type of gas supplied to the reactor.

Before the water is supplied to the reactor, it can be ventilated to remove oxygen and other gases. The water can be treated with stabilizing agents, additives and/or supplied with small seeds of hydrate crystals (as stated above). The stabilizing agents increase the storage and transportation ability of the hydrate particles with embedded gas. These agents may be produced from hydrocarbon fractions separated from the starting material, either from natural gas or natural gas together with other hydrocarbons. The additives can be compounds that decrease the surface tension of water, thus increasing the reaction rate for the formation of gas hydrate.

As set forth above, the hydrate forming reaction is exothermic, but the contribution from expansion of gas by utilizing the Joule-Thomson effect to the total cooling requirement is small. Accordingly, the hydrate reactor must be cooled, either directly or indirectly. Direct cooling can, for example, be provided by circulating excess gas through an external refrigeration plant. In such cases, a need for an additional compressor will arise. Indirect cooling can be accomplished with a cooling jacket or cooling elements, e.g. provided with a coolant from a closed circuit cooling system in the form of a refrigeration unit. The mass and energy balance of the stream supplied to the reactor vessel is preferably adjusted to convert the substantial part of the water to hydrate particles, thus operating the process with excess gas. The reactor vessel can also be operated with excess water, and then, water must be separated away. The process can also have gas and water in excess. However, operating the reactor with excess gas is preferred. In this way, dry hydrates are formed that will decrease the risk of accumulation of hydrate and blocking of the reactor outlet.

Minor amounts of gas and any water can flow along with the hydrate particles. The un-reacted and removed components of gas and flowing water can be recirculated; water is typically recirculated and combined with the fresh water feed and separated gas is compressed, cooled and passed directly back to the reactor. Compressing the recirculated gas to a pressure slightly above the reactor pressure is sufficient so that the gas easily flow into the same. The recirculated streams can also be treated with additives and further treated with respect to production of hydrate particles. Unreacted gas from the reactor is optionally compressed and supplied to another similar system operated at a higher pressure. The hydrate particles with embedded gas are transported, as described above, optionally to equipment for agglomerating or collecting the small particles to larger particles. The first hydrate particles are cooled and/or refrigerated in a refrigeration unit prior to entering the agglomeration step. Cooling and freezing can be accomplished by pressure change, direct supply of cooled/refrigerated gas and/or indirect heat exchange. The purpose of the agglomeration is to decrease the total volume of the hydrate and simultaneously provide more volume for gas storage in the particle pore volume. The compression or "agglomeration" can occur at pressure and temperature conditions chosen to achieve an optimum gas content and particle stability, i.e. the pressure and temperature must be at the high pressure side/low temperature side of the equilibrium curve for hydrate formation. Additives can be mixed with the hydrate particles to improve their properties. Depending on the process conditions chosen, the total mass percent of gas can in general be in the range from 10 to 40 percent of the particle weight. After the agglomeration, the hydrate particles can be cooled and/or refrigerated, thus retaining the total gas content inside the hydrate particle. The diameter of the compressed hydrate particles varies with the method used for agglomeration and the degree of compression desired, but a typical particle diameter for agglomerated natural gas hydrate particles is, for example, 2–20 mm. Likewise, the density will vary with the agglomeration method and degree of agglomeration, but a typical density is in the range from 850 to 950 kg/$m^3$.

Such gas containing hydrate particles can be produced at offshore platforms or onshore. The platforms can be temporary or permanent. Onshore, the hydrate particles can be produced at a location close to hydrocarbon sources or other locations. The gas supplied in this way can be natural gas or natural gas together with other constituents. It can also be pollution gas to be transported away for further treatment, loops required to maintain hydrate formation and freezing conditions. These temperatures allow the use of conventional, post-Montreal Protocol refrigerants (e.g. HFA-134). Natural gas feed is available at 660 psig, 100° F., consistent with process economics studies of LNG technology "LNG & Methyl Fuels", SRI Process Economics Program Report #103, Sept. 1976.

What is claimed is:

1. A process for continuously producing clathrate hydrate comprising the steps of:

(a) pressurizing a hydrate-forming gas to an elevated pressure and cooling said hydrate-forming gas below the gas-water-hydrate equilibrium point at said elevated pressure;

(b) cooling liquid water below the gas-water-hydrate equilibrium temperature for said elevated pressure;

(c) charging said hydrate-forming gas at said elevated pressure into a reaction zone which contains a rotating drum which provides a moving surface;

(d) atomizing said water in said reaction zone in contact with said hydrate-forming gas to form gas hydrates in said reaction zone;

(e) depositing said gas hydrates on said moving surface; and (f) collecting said gas hydrates from said moving surface.

2. The process of claim 1 further comprising spraying said deposited gas hydrates of step (e) with wash water and drawing at least a portion of said wash water through said moving surface.

3. The process of claim 1 wherein said collecting step (f) further comprises scraping hydrate from said moving surface.

4. The process of claim 1 wherein said collecting step (f) further comprises crushing said hydrate.

5. The process of claim 4 further comprising flowing said crushed hydrate in contact with an inert gas.

6. The process of claim 5 wherein said inert gas is substantially dry.

7. The process of claim 1 wherein said moving surface comprises an additive to promote hydrate formation.

8. The process of claim 7 wherein said additive is a zeolite.

9. The process of claim 1 wherein said moving surface is water permeable.

10. A process for producing gas hydrates, comprising:

pressurizing a hydrate-forming gas to an elevated pressure and cooling the hydrate-forming gas below the gas-water-hydrate equilibrium point at the elevated pressure;

cooling liquid water below the gas-water-hydrate equilibrium temperature for the elevated pressure;

charging the hydrate-forming gas and the water into a reaction zone, wherein the hydrate-forming gas and the water form gas hydrates in the reaction zone;

depositing the gas hydrates on a moving surface of a rotating drum; and positioning a doctor blade proximate to the moving surface and removing the gas hydrates from the moving surface using the doctor blade.

11. The process according to claim 10, further comprising crushing the gas hydrates after the gas hydrates are removed from the moving surface.

12. The process according to claim 10, further comprising transporting the gas hydrates away from the reaction zone after the gas hydrates are removed from the moving surface.

13. The process according to claim 10, further comprising washing the deposited gas hydrates on the moving surface with wash water.

14. The process according to claim 13, wherein at least a portion of the wash water is drawn through the moving surface.

15. The process according to claim 10, further comprising, after removing the gas hydrates from the moving surface:

passing the gas hydrates through a pair of rotating rollers or grinders; and transporting the gas hydrates away from the reaction zone.

16. The process according to claim 15, wherein the pair of rotating rollers or grinders creates a seal between the reaction zone and an area outside the reaction zone.

17. The process according to claim 16, further comprising passing the gas hydrates through a second pair of rotating rollers or grinders after the gas hydrates are transported away from the reaction zone.

18. The process according to claim 17, wherein the second pair of rotating rollers or grinders creates a seal between a volume through which the gas hydrates are transported and an area outside the volume.

19. The process according to claim 15, further comprising passing the gas hydrates through a second pair of rotating rollers or grinders after the gas hydrates are transported away from the reaction zone.

20. The process according to claim 19, wherein the second pair of rotating rollers or grinders creates a seal between a volume through which the gas hydrates are transported and an area outside the volume.

* * * * *